United States Patent [19]
Yagita et al.

[11] Patent Number: 6,081,324
[45] Date of Patent: Jun. 27, 2000

[54] FOREIGN MATTER DETECTING SYSTEM

[75] Inventors: Kiyoshi Yagita; Hirotsugu Kobayashi, both of Minato-ku, Japan

[73] Assignee: Scan Technology Co., Ltd., Tokyo, Japan

[21] Appl. No.: 09/310,955

[22] Filed: May 13, 1999

Related U.S. Application Data

[63] Continuation-in-part of application No. 09/245,306, Feb. 5, 1999, which is a continuation-in-part of application No. 09/100,894, Jun. 22, 1998.

[51] Int. Cl.[7] .................................................. G01N 11/00
[52] U.S. Cl. .......................................... 356/237; 356/239
[58] Field of Search ............................... 356/73, 237, 239

[56] References Cited

U.S. PATENT DOCUMENTS

| | | | |
|---|---|---|---|
| 4,906,101 | 3/1990 | Lin et al. | 356/442 |
| 4,909,930 | 3/1990 | Cole | 209/564 |
| 5,072,108 | 12/1991 | Ishikawa | 250/223 |

*Primary Examiner*—Robert H. Kim
*Assistant Examiner*—Andrew H. Lee

*Attorney, Agent, or Firm*—Sughrue, Mion, Zinn, Macpeak & Seas, PLLC

[57] ABSTRACT

For use in the production line for manufacturing a liquid product such as a beverage or a liquid drug, a system is provided for detecting foreign matter contained in the fluid which is being conveyed at high speed in a conduit and automatically removing the same. The system comprises an inspection station which is connected to the conduit and of which the inspection window for detecting foreign matter is made of at least a transparent material, an illuminating means for illuminating the subject to be inspected with light directed through the inspection station, an imaging means for picturing the subject to be inspected by directing an intensity of light to the inspection window and receiving transmission or reflection of the light, a detecting means for comparing the signal level where a part indicative in which the level of the video signal is sharply changing is emphasized and processed with a reference level for the subject to be inspected to detect the foreign matter contained in the fluid. When the foreign matter is detected by the detecting means, the fluid is temporarily switched to a branch of the tubular conduit by the open and close action of a control valve to systematically discharge a portion of the fluid where the foreign matter is present.

19 Claims, 9 Drawing Sheets

FIG. 10

FOREIGN MATTER DETECTING SYSTEM

This application is a continuation-in-part of Ser. No. 09/245,306 filed Feb. 5, 1999 which is a continuation-in-part of Ser. No. 09/100,894 filed Jun. 22, 1998.

BACKGROUND OF THE INVENTION

1. Technical Field

The present invention relates to a foreign matter detecting system for detecting foreign matters contained in a liquid product such as a beverage or a liquid drug and particularly, a foreign matter detecting system for examining at real time whether or not a flow of fluid running in a tubular conduit carries foreign matters.

2. Prior Art

As the applicable food sanitary laws are based on HACCP and the PL (product liability) regulations are enforced, it will be obligatory to avoid any undesired incident, such as microbial contamination or entrance of impurities, which may occur in all steps of food quality control from the production and process of food and drug products to storage, shipment, and consumption of the products and to increase the cleanliness and the safety of such products.

HACCP stands for hazard analysis of critical control points which has been developed in U.S.A. and is known throughout the world as one of the best sanitary control system methods. The HACCP is intended for evaluating the safety of products in all manufacturing processes as compared with conventional sanitary control methods where the final products are a subject to be inspected the HACCP particularly focuses on the preventive quality control in each process and consists mainly of two major sections: hazard analysis and critical control points. Any possibility of hazardous incidents such as microbial contamination which may occur in each step of the manufacturing and processing of foods and the storage and shipment of products before the end consumers is reviewed and analyzed through determining the critical control points for preventive actions and the control standards and constantly monitoring and checking the records of control whether or not the requirements are fulfilled within allowance. Also, other hazardous items are controlled by the pre-requisite program to prevent any adulteration in the process and to improve the safety quality of products.

In manufacturing and processing plants for liquid products (e.g. beverages and liquid drugs), heating and pasteurization processes are used for preventing microbial contamination in the production line and removal of impurities with cyclone separators or the like is implemented for adulteration. When the products have been packed in containers such as cans or bottles, they are visually inspected for final, before-delivery checking. More specifically, manufacturing and processing plants for liquid products such as soft drinks or fruits and vegetable juice yield a very large quantity of products by transferring liquid materials from steps of removal of impurities to tanks and then conveying them via tubular conduits (referred to as pipelines hereinafter) to a filler where a stream of containers, such as cans or bottle, are automatically filled with the mixed materials.

In such manufacturing and processing plants, the products in process may be adulterated by foreign matters which are substantially classified in the term of source into: "material impurities" contained in the materials, "environmental impurities" entering the materials not packaged, and "equipment impurities" generated in manufacturing equipment in the production line. The removal of impurities from the liquid product which are greater in specific gravity than the liquid product can be implemented by the use of a cyclone separator or the like. The impurities, which are greater in particle size than the materials can be removed by filtration. Those are common processes for removing foreign matters from the liquid products before the major process in manufacturing steps of the conventional manufacturing and processing plants as well as the final inspection and test for ensuring the safety of the products.

However, there is still potential for adulteration with impurities in the manufacturing/processing step even if the preprocess inspection and the removal of impurities from the materials have been carried out. For example, the liquid materials may be contaminated with environmental and equipment impurities while being conveyed from their respective tanks via pipelines to the filler station where they are packaged into containers such as cans. For compensation, the liquid products such as tea or milk are filtered by a fairly fine filter to remove minute particles with simplicity. Fiber matters are likely to block up a screen of the filter and may be removed by the filter with much difficulty. The material including particles of different sizes is filtered by a series of filters to remove impurities which are greater in size than the particles but equipment impurities added after the material stage will rarely be removed by filtration. Visual inspection is not applicable to the liquid product running in the pipeline and makes the removal of impurities impossible.

In practice, the liquid product including fibers and particles is examined at its material stage by visual inspectors viewing material solutions and additives in the tanks and impurities found can only be removed by manual process. While being conveyed via the pipeline to the filler station where it is packaged into containers, the liquid product is not subjected to the inspection for adulteration and the removal of impurities.

SUMMARY OF THE INVENTION

The present invention has been developed in view of the foregoing aspects and its object is to provide a foreign matter inspecting system for detecting foreign matters contained in a fluid running at high speed in a conduit and automatically removing the same and for use in a production line for manufacturing liquid products such as beverages and liquid drugs.

For achievement of the above object of the present invention, a foreign matter detecting system for detecting a foreign matter contained in a fluid of liquid which is a subject to be inspected and is conveyed in a tubular conduit, comprising: an inspection station which is connected to the tubular conduit and of which the inspection window for detecting foreign matter is made of at least a transparent material; an illuminating means for illuminating the subject to be inspected with light directed through the inspection station; an imaging means for picturing the subject to be inspected by directing an intensity of light to the inspection window and receiving transmission or reflection of the light; and a detecting means for comparing the signal level where a part indicative in which the level of the video signal is sharply changing is emphasized and processed with a reference level for the subject to be inspected to detect the foreign matter contained in the fluid.

In addition, the present invention is improved by the features that a branch from the tubular conduit is connected to the downstream side of the inspection station via a control valve for discharge of the foreign matter and if the foreign matter is detected, the control valve performs an open/close action to connect the flow of the fluid to the branch for removal of a portion of the fluid in which the foreign matter is contained, that the reference level is a level defined in an analog slice level range which is determined by shifting the waveform of an analog video signal produced through scanning with the imaging means by two widths of threshold to both the high and low level sides respectively and the detecting means is arranged to continuously examine the analog video signal through scanning and determine whether or not the signal level after the emphasizing process is within the analog slice level range for detecting foreign matters at real time, that the detecting means stops output of its detection in response to a pause in the action of a filler device for filling product containers with the fluid, that the subject to be inspected is a liquid mixture of different materials and the inspection station is provided across the tubular conduit at the downstream of the mixing of the materials over their respective channels, that the inspection station including the inspection window has a cylindrical shape of which the inner diameter is identical to the inner diameter of the tubular conduit, that the cylindrical shaped inspection window has an annular mirror surface provided in a cross section of a wall thereof and tilted at such an angle that the intensity of light emitted from a light source is reflected on the mirror surface to linearly run throughout the wall of the cylindrical shaped inspection window, hence acting as an illuminant which illuminates with its annular mirror surface reflecting the intensity of light emitted from the light source by the illuminating means, that the imaging means incorporates a group of photo-sensor units arranged at equal intervals in a circle about the cylindrical shaped inspection window for allowing the detecting means to inspect the subject from different directions radically of the cylindrical shaped inspection window, that at least the inspection window of the inspection station is arranged flat and the cross sections at the joint to the tubular conduit and at the inspection window of the inspection station are identical to the cross section of the tubular conduit, that the wavelength and intensity of the light emitted from a light source of the illuminating means are predetermined corresponding to the characteristics of the subject to be inspected, and the illuminating means discharges the light having by specific wavelength and intensity based on the setting value for the subject to be inspected, that the illuminating means discharges the light having a plurality of wavelengths corresponding to the characteristics of the subject to be inspected, that comprising a recording means to record the detection situation of impurities, that the duration of open/close action of the control valve is controlled based on parameters including the velocity of the fluid preset at each subjects to be inspected, that the duration of open/close action of the control valve is controlled with the use of a sensor which monitors and measures the current velocity of the fluid of liquid, that a distal portion of an optical fiber is located on the circumference of the cylindrical shaped inspection window to uniformly emit the light from its light emitting end to the annular mirror surface, and that further including a flow sensor which is provided adjacent to the subject to be inspected, and said flow sensor detects the pause action of the filler device based on detecting information of presence/absence of the fluid.

In addition, the object of the present invention may be achieved more effectively by the features that further comprising a turbulence relieving tank provided on the upstream side of the inspection station for receiving a flow of the fluid from the upstream and relieving a turbulence in the flow before releasing out the fluid, that further comprising a turbulence relieving tank provided on the downstream side of the inspection station for receiving a flow of the fluid from the inspection station and relieving a turbulence in the flow before releasing out the fluid, and that two or more of the inspection stations are connected in parallel while a first turbulence relieving tank is provided on the upstream side of the parallelly connected inspection stations for receiving a flow of the fluid from the upstream and relieving a turbulence in the flow before delivering separate flows of the fluid to the corresponding inspection stations and a second turbulence relieving tank is provided on the downstream side of the parallelly connected inspection stations for combining flows of the fluid received from their respective inspection stations and relieving a turbulence in the flow before releasing out the fluid.

BRIEF DESCRIPTION OF THE DRAWINGS

In the accompanying drawings.

DESCRIPTION OF PREFERRED EMBODIMENTS

The present invention is directed towards detecting foreign matters contained in a flow of liquid which runs at high speed in a conduit of a production line for producing liquid products, such as beverages or liquid drugs intake by human bodies and systematically removing them without interrupting the operation of the production line. More specifically, according to the present invention, various foreign matters produced in a procedure of production/process, including "material impurities" not removed during the inspection of materials, "environmental impurities" possibly entering before the production line, and "equipment impurities" produced by manufacturing machines during the production, are detected and systematically removed through discharging their contained solution from branch lines, whereby the potential for health hazard through adulteration will be prevented and the safety attributes of products will be improved.

Preferred embodiments of the present invention will now be described in more detail referring to the accompanying drawings. A foreign matter detecting system of the present invention is applicable not only to the liquid products, such as beverages or liquid drugs, intake by human bodies but also as a common fluid impurity detecting system. The following description is based on the application to a plant for manufacturing/processing liquid foods or drugs.

Figure 1:
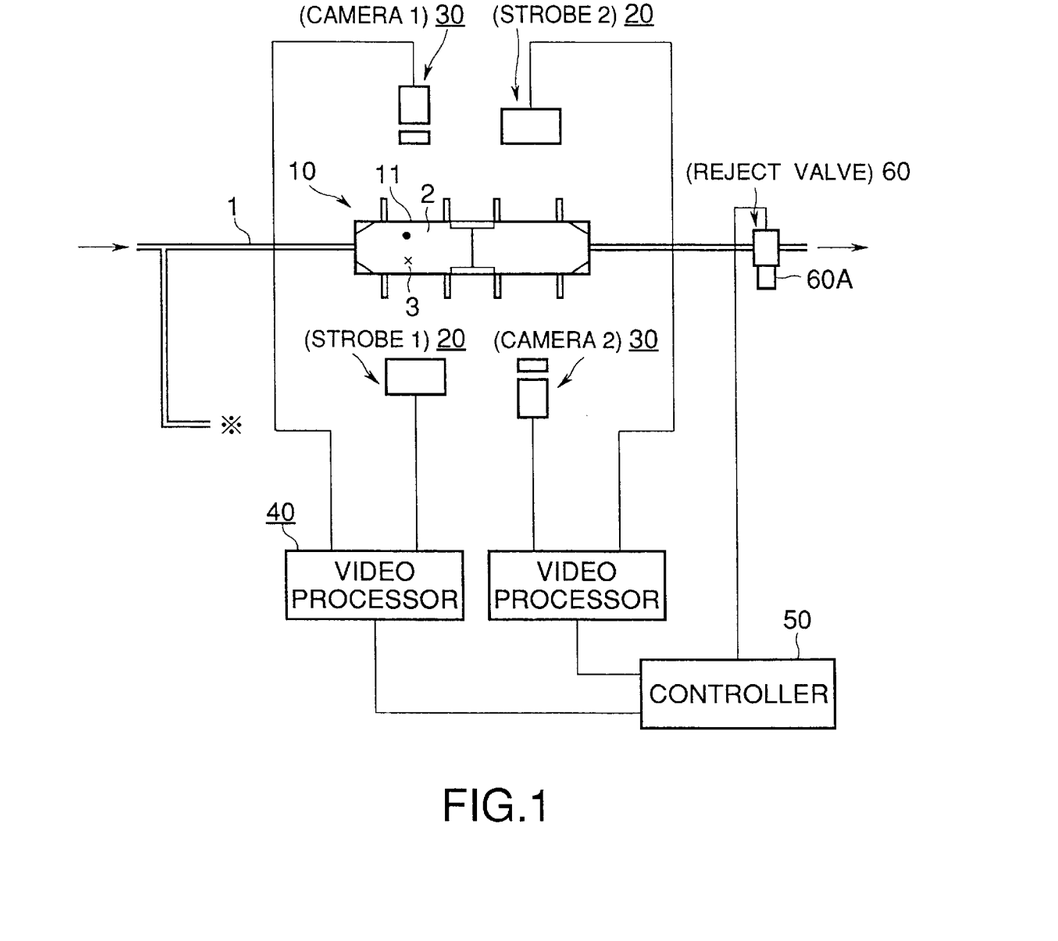
FIG. 1 is a block diagram showing a fundamental arrangement of a foreign matter detecting system according to the present invention.

FIG. 1 illustrates a fundamental arrangement of the foreign matter detecting system according to the present invention. As shown, a window for detecting impurities contained in a fluid 10 (referred to as an inspection window hereinafter) is provided in a pipeline 1 where a material fluid runs. The pipeline 1 is connected at its downstream to a branch line (a discharge line for removal of impurities) 60A via a control valve for removal of the impurities (a reject valve) 60. The inspection window 10 is implemented by a tubular conduit which is identical in the inner diameter to the pipeline 1 (e.g. having 40 mm of an inner diameter) and made as the whole of a transparent material such as glass or transparent polymer. In FIG. 1, a portion of the window 10 is enlarged as a transparent tube segment 11. More specifically, the two inspection windows 10 are joined to a single unit in this embodiment. One or more imaging devices (namely, CCD cameras) 30 are provided in a circle about the transparent tube segment 11 of the inspection window 10 for picturing a flow of fluid 2 running across the inspection window 10 as receiving reflection of the light emitted from an illuminating device 20 (consisting of strobe 1 and strobe 2 as shown in FIG. 1).

It is assumed that the subject to be inspected is a liquid or fluid of relatively transparent material. When the fluid 2 has a level of transparency enough to allow the light from the illuminating device 20 to transmit across the transparent tube segment 11, any foreign matter 3 contained in the fluid 2 can be detected without difficulty. If the fluid to be inspected is translucent allowing the light to reach a center of the transparent tube segment 11 but not transmit through the same, its flow can be monitored for detection of any impurity by the imaging devices 30 arranged in a circle at equal intervals about the transparent tube segment 11. The imaging device 30 shown in FIG. 1 has a shooting range in a radial direction greater than the diameter of the transparent tube segment 11 and two (a camera 1 and a camera 2) of them are disposed on opposite sides of the transparent tube segment 11 and spaced from each other lengthwisely of the transparent tube segment 11 (or not spaced lengthwisely but aligned in a circle about the transparent tube segment 11) so that the entire flow of the translucent fluid running in the transparent tube segment 11 can be pictured. It is also possible that the flow of a fluid having non or a lower level of transparency that hardly allows the transmission of light to the center of the transparent tube segment 11 is inspected in at least its outer surface regions by a group of the cameras or photo units 30, which are arranged at equal intervals in a circle about the transparent tube segment 11, receiving reflections of the light from different directions.

An image processor 40 is provided for receiving video signals from the imaging devices 30 and comparing their signal level with a reference level predetermined from the fluid to be inspected to detect any foreign matter contained in the fluid. More particularly, a fluid material, such as a beverage or a liquid drug, to be inspected is substantially uniform in both the transitivity and the reflectivity of light when containing no impurities and its video signal will thus be constant in the signal level. As an average or a range of the signal levels is designated as a reference level, a difference from the reference level of the video signal may be detected as the presence of impurities. For example, the reference level of a video signal produced by picturing a flow of juice including fibers and particles of fruits or vegetables (or a mixture of them) is predetermined and when a critical change in the video signal from the reference level is detected, it is judged that the flow (or the mixture) contains impurities. This action may however be retarded by processing relevant image data digitized and saved in a line memory or a frame memory. In the video processor 40, an analog video signal produced by the scanning of the imaging device 30 is compared with the reference level for inspection of consecutive analog images. For example, when a beverage is manufactured and conveyed at a rate of 8 to 10 tons per hour in the pipeline, its flow is substantially 1 to 2 meters per second depending on the inner diameter of the pipeline or the feeding velocity. The flow can only be monitored by a known image processing method in which frames of sampled and quantified digital image, resulting in dropouts of the inspection due to the pertinent data decimation.

According to the present invention, for detecting impurities contained in the flow of fluid which runs at a high speed, a time succession of the analog video signals is produced by the imaging device 30 and the signal level where a part indicative in which the level of the analog video signal is sharply changing is emphasized and processed is compared with the analog slice level range determined by shifting the waveform of a not-emphasized video signal by two thresholds S1 and S2 to the high and low level sides respectively. More particularly, foreign matter in the fluid running at high speeds in the conduit can be detected at real time by scanning a time series of analog images to continuously examine the video signal before sampled and quantized whether or not the its level after the emphasizing is within the analog slice level range determined at real time. The emphasizing the signal and the determining the analog slice level range will be explained later in conjunction with the waveform representations.

The video processor 40 includes a controller connected via an input/output interface to the illuminating devices 20 and a controller 50 for the reject valve (the control valve for removal of impurities). A critical portion of the fluid containing the impurities is discharged from the branch line 60A by the controller temporarily shifting and connecting the outlet of the control valve 60 to the branch line 60A. Since the velocity of the fluid 2 passing the inspection window 10 is uniform, the time of the impurities arriving at the reject valve 60 and the duration of open/close action of the valve 60 (or the period of shifting the flow) can be predetermined at each inspection procedure according to parameters including the distance between the inspection window 10 and the reject valve 60 and the velocity of the fluid to be inspected. It is noted that the flow is varied in the velocity and may momentarily stall in turbulence depending on the specific gravity and the shape of impurities and the open/close action of the reject valve 60 should duly be adjusted in consideration of the variations of the flow. The open/close action of the reject valve 60 may be controlled not by presetting its operating time but with the use of a sensor(s) which monitors and measures the current velocity of the flow.

Also, the controller of the video processor 40 controls illumination of the illuminating device other than the discharge of impurities and cooperates with a filler device for filling a container with the fluid to complete a product. In this embodiment, the controller is responsive to a control signal from the filler device indicative of a pause in the action of the filler device and stops the output of detection signals (of the result of inspection) in response to the pause action of the filler device. A flow sensor may be provided adjacent to the inspection window 10 for detecting the absence of a fluid which represents the pause action of the filler device.

An improvement of the illuminating device according to the present invention is explained. As described, the inspection window 10 mounted across the pipeline 1 for conveying the fluid is made of a transparent tube segment which can transmit beams of light. While the fluid running in the transparent tube segment is illuminated from radial directions, it is necessary to locate the photosensitive devices to optimum or limited positions in consideration with refractive index of the fluid and reflectivity/refractive index of the transparent tube segment. Also, the reflection of light from impurities is not always favorable to be perceived and may generate an inspection error. According to the present invention, the transparent tube segment of the inspection window is modified with its wall made of an illuminant.

Figure 2:
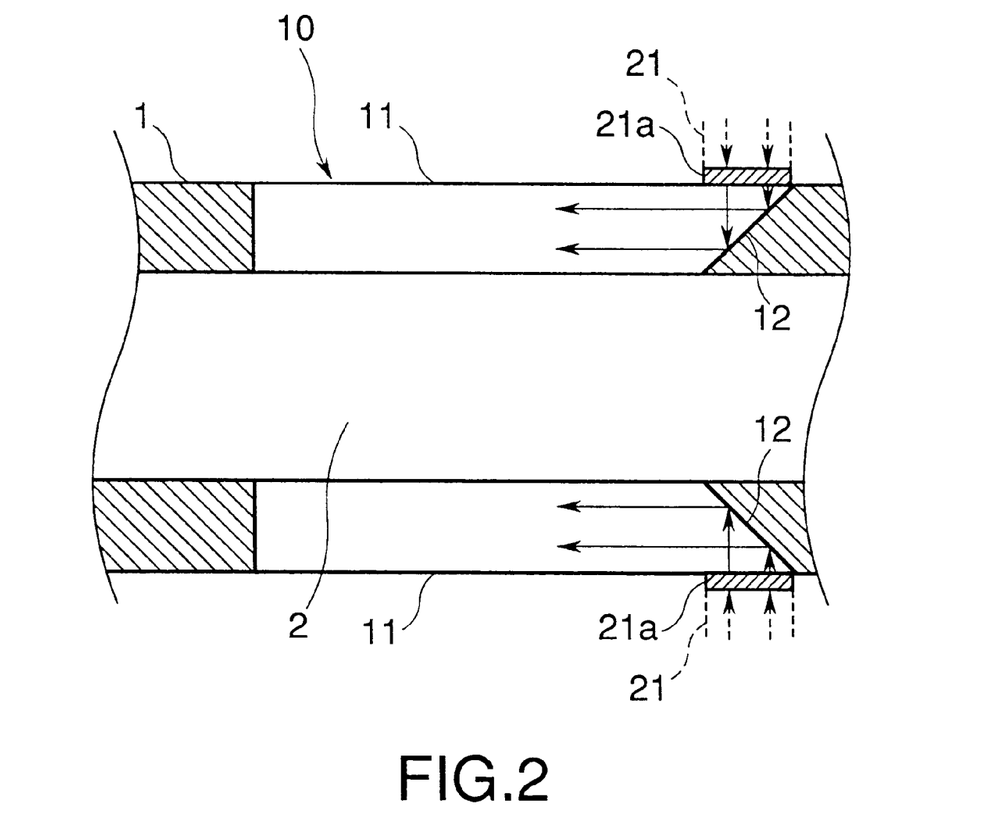
FIG. 2 is a cross sectional view showing schematically an installation of an illuminating device provided in the embodiment.

FIG. 2 is a cross sectional view showing schematically a combination of the illuminating device 20 and the transparent tube segment 11 of the inspection window 10 of FIG. 1. As shown, an annular mirror surface 12 arranged at an angle (the side of a truncated conical form) is provided in the cross section of the transparent tube segment 11 for reflecting the light from a light source and directing it to run linearly through the wall of the transparent tube segment 11. As the light (emitted from the light emitting end 21a of a light emitter 21 shown in FIG. 2) has fully been reflected on the annular mirror surface 12, it linearly runs throughout the wall of the transparent tube segment 11 which thus becomes an illuminant. This allows the fluid 2 to be illuminated uniformly and its impurities to be detected throughout the transparent tube segment 11. Also, the freedom of locating the imaging devices will be increased. Preferably, the light emitter 21 is a distal portion of an optical fiber, as shown in FIG. 2, which is located on the circumference to uniformly emit the light from its light emitting end 21a to the mirror surface 12. The wavelength and intensity of the light emitted from a light source provided at the other end of the optical fiber are predetermined corresponding to the characteristics of a subject to be inspected. The light may have a plurality of wavelengths for providing a higher degree of difference in the transitivity and the reflectivity of the subject.

Figure 3:
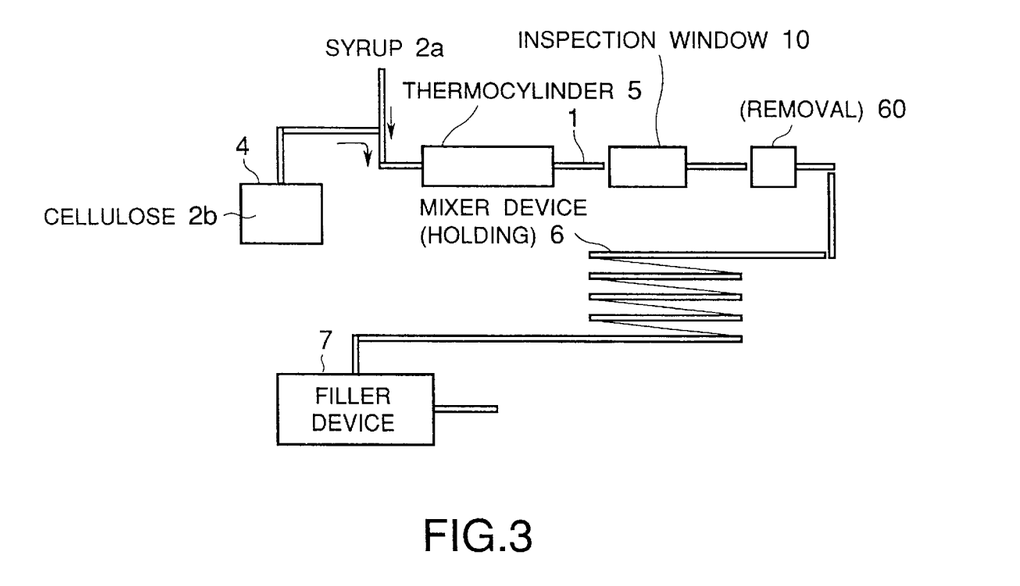
FIG. 3 is a block diagram showing a modification of the foreign matter detecting system.

A modification of the foreign matter detecting apparatus in a production line for mixing different materials to a product is explained. FIG. 3 illustrates schematically the production line for manufacturing a common beverage which is a mixture of syrup 2a and cellulose 2b of food plant (fruits or vegetables).

In the manufacturing of a mixture beverage, different materials contained in their respective tanks 4 are conveyed along conduits to a mixer device (holding) 6 for producing a mixture which is then supplied via the pipeline 1 to the filler device 7 for filling containers, such as cans or bottles, with the mixture to have beverage products.

In the embodiment shown in FIG. 3, the detection and removal of impurities are carried out in a preparation step between the joining of fluid materials to the pipeline 1 and the transfer from the pipeline 1 to the mixer device 6. The inspection window 10 for detecting impurities is provided at a desired location across the pipeline 1 after the joining and the reject valve 60 is located at the downstream of the inspection window 10 for removal of the impurities. In particular, a thermocylinder 5 is provided at the upstream of the inspection window 10 for measuring the temperature in the preparation step. The history of the temperature at the preparation step as well as the detection and removal of impurities are recorded by the controller of (a computer for) the foreign matter detecting system.

Figure 4:
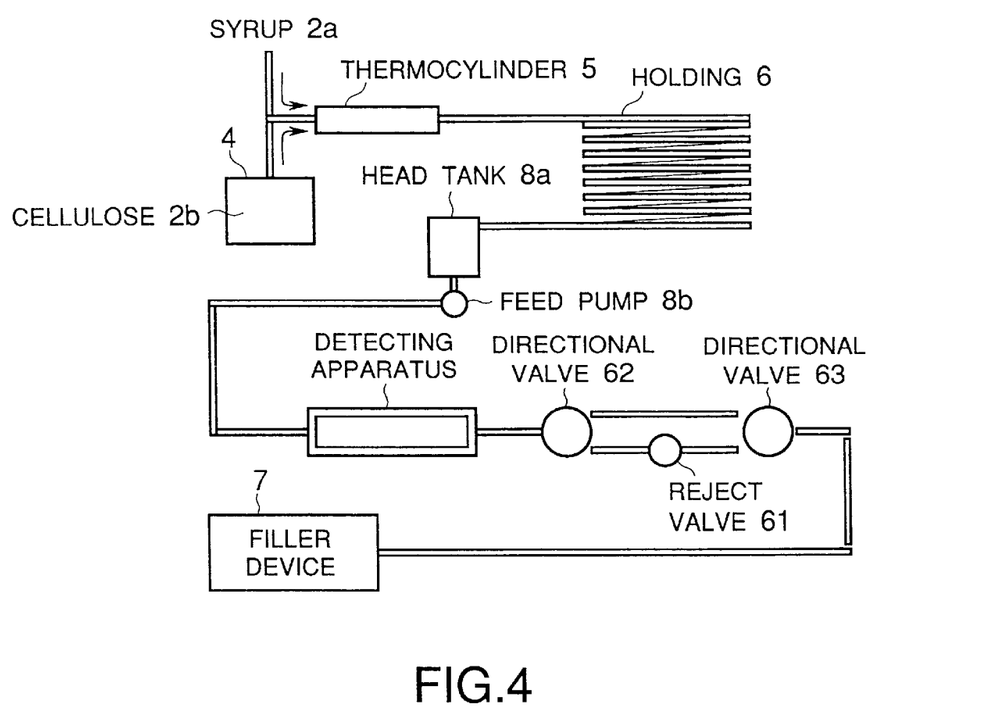
FIG. 4 is a block diagram showing another modification of the foreign matter detecting system.

FIG. 4 illustrates another modification of the foreign matter detecting apparatus in which the detection and removal of impurities is implemented between a mixer device 6 and the filler device 7 and more particularly, in a preparation stage with a head tank 8a and a feed pump 8b connected at the downstream of the mixer device 6 prior to the filler device 7. While the fluid after mixture in the mixer device 6 is to be inspected, the detection of impurities is carried out by the same manner as of the system shown in FIG. 3 where the fluid is inspected before the mixer device 6. As shown in FIG. 4, the pipeline has a bypass between two directional valves 62 and 63 and a reject valve 61 is connected across the bypass. This allows a portion of the fluid containing impurities to be shifted to the bypass by the action of the directional valves 62 and 63 and discharged without difficulty from the reject valve 61 opened. When the impurities have been removed, the fluid is shifted to the main line and the reject valve 61 is closed.

Figure 5:
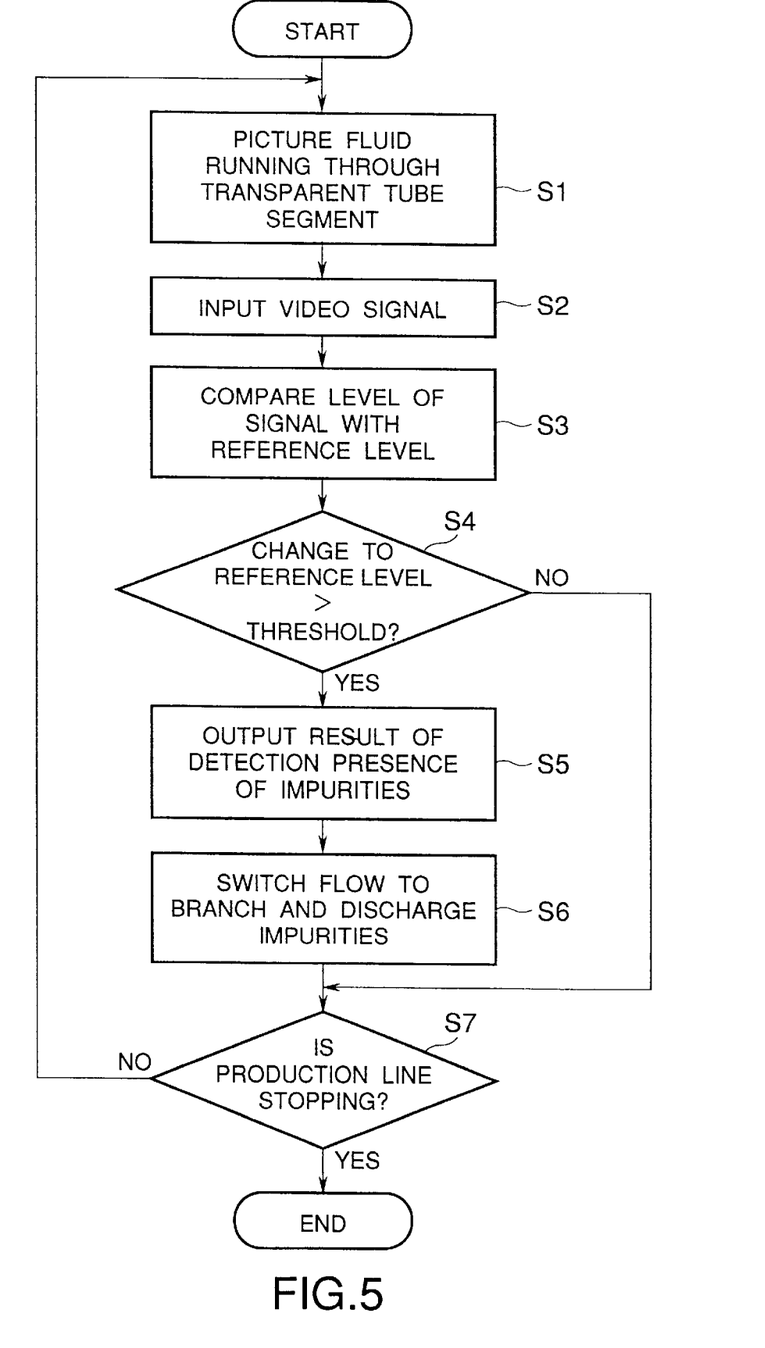
FIG. 5 is a flowchart of an operation of the system of the present invention.

The operation of the system of the present invention shown in FIG. 1 will be described referring to a flowchart of FIG. 5.

The fluid 2 running through the transparent tube segment 11 is pictured by the imaging device 30 (Step S1). This is followed by the video processor 40 receiving a video signal from the imaging device 30 (Step S2), and while the part where the signal level is sharply changing is emphasized and processed, the analog slice level range is determined over the not-emphasized video signal and it is examined whether or not the level of the emphasized analog video signal is within the analog slice level range. The video signal from the imaging device 30 is an analog signal which is continuous with time. With line sensors, their output signals or with a two-dimensional area sensor, its horizontal scanning signal is received as the analog video signal and it is continuously examined whether or not the emphasized analog video signal is within the analog slice level range (Step S3).

Figure 6A:
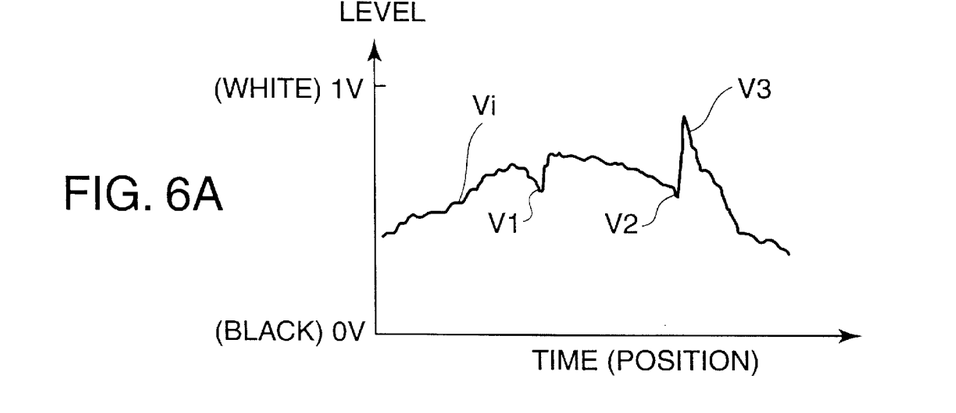
FIGS. 6A–C is a diagram explaining an image data process according to the present invention.
Figure 6B:
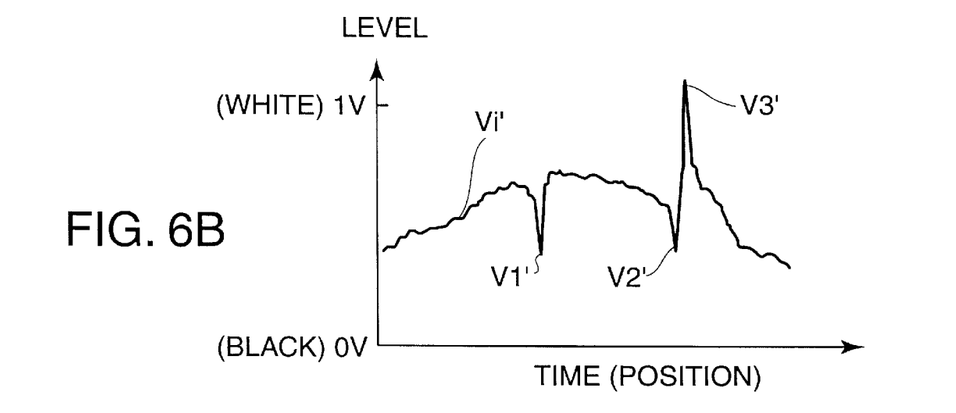
Figure 6C:
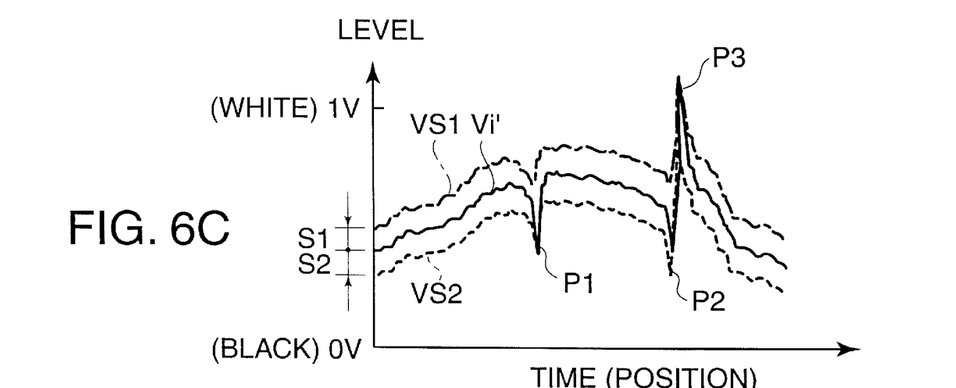

FIGS. 6A, 6B, and 6C illustrate a waveform of the analog video signal Vi produced by scanning with the imaging device 30, a waveform of the emphasized analog video signal Vi', and their relation to two analog slice levels VS1 and VS2. Referring to the figures, an action of the detection will be explained. When the fluid contains foreign matter, the signal level is sharply changed as denoted by V1, V2, and V3 in FIG. 6A (three locations in this example) representing change in the luminance.

In the image processor 40, the video signal Vi is differentiated and compared with its threshold. Its portions V1, V2, and V3 where the differential is greater or the signal level is sharply changed as shown in FIG. 6A (in this example, the luminance is sharply changed) are amplified and emphasized. The emphasizing is done at real time and its resultant emphasized signal Vi' shown in FIG. 6B is used for detecting foreign matter. According to the present invention, the waveform (of the not-emphasized video signal shown in FIG. 6A) is shifted by the thresholds S1 and S2 (S1=S2 in this example) to the high and low level sides respectively as shown in FIG. 6C to determine two, first and second, analog slice levels VS1 and VS2. The two (differential) slice levels define the analog slice level range which is then used as a reference level range for detecting foreign matter.

A detector in the image processor 40 examines whether or not the emphasized analog video signal is within the analog slice level range (Step S4). When the signal is out of the analog slice level range, it is judged that foreign matter is present and a resultant output (for example, "0" indicating a normal condition and "1" indicating the detection of foreign matter) is released via an A/D converter. In FIG. 6C, P1, P2, and P3 represent the presence of foreign matter. Returning back to FIG. 3, there are predetermined the two thresholds S1(a) and S2(a) for a base fluid or "syrup" 2a and the two thresholds S1(b) and S2(b) for an additive to the base fluid or "cell" 2b provided in the form of fiber or particles. When the level of each emphasized analog signal is not within the corresponding analog slice level range, it is judged that foreign matter is present and its detection signal indicating the presence of foreign matter is released (Step S5).

The result of detection is received by the controller which if impurities are present, switches the flow to the branch 60A via the control panel 50 and opens the control valve 60 for a predetermined period of time to discharge the impurities (Step S6). The procedure from S1 to S6 is repeated while the filler device is actuated (i.e. the production line is turned on) and when the filler device is switched off (Step S7), the detection of impurities is terminated and the procedure moves into a standby mode.

Although the inspection station of the pipeline in the inspection window is at least made of a transparent material in the embodiments, it is essential that the inspection window is transparent and the pipeline may be made of a transparent material in its entirety. The inspection station is not limited to the transparent tube segment which is identical in the inner diameter to the pipeline but may be implemented by a joint of a cone shape between two pipelines which is greater in the inner diameter than the pipelines.

When the inner diameter at the inspection station is greater than that of the conduit, the imaging area can be increased. Its advantage is that the present invention is applicable to a system where the diameter of conduits is small, while its disadvantage is that the diameter difference alters the speed of flow hence creating an eddy of turbulence such as a whirlpool where foreign matter to be detected may be trapped. It is thus preferred that every part of the inspection station across which the fluid runs is arranged identical in the cross section to the conduits and its inspection window is made flat.

Figure 7A:
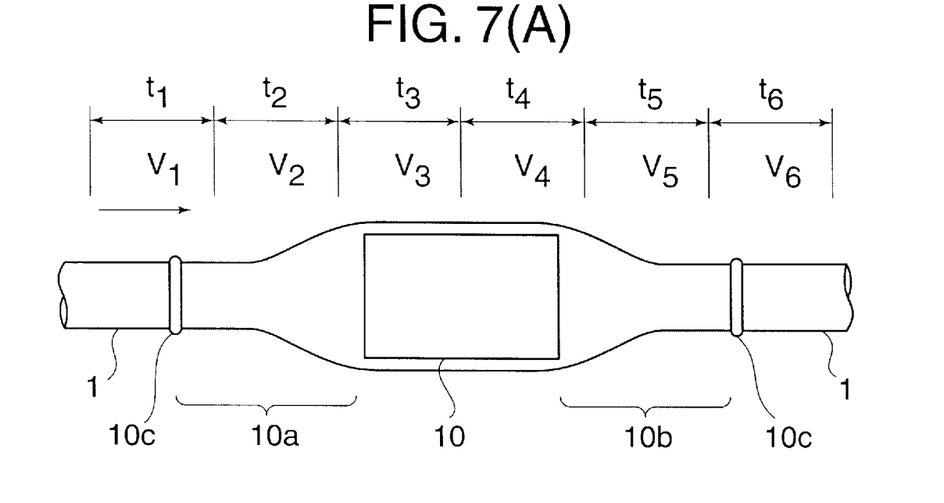
FIGS. 7A and 7B are a plan view and a partially cross sectional side view of another arrangement of the inspection station according to the present invention.
Figure 7B:
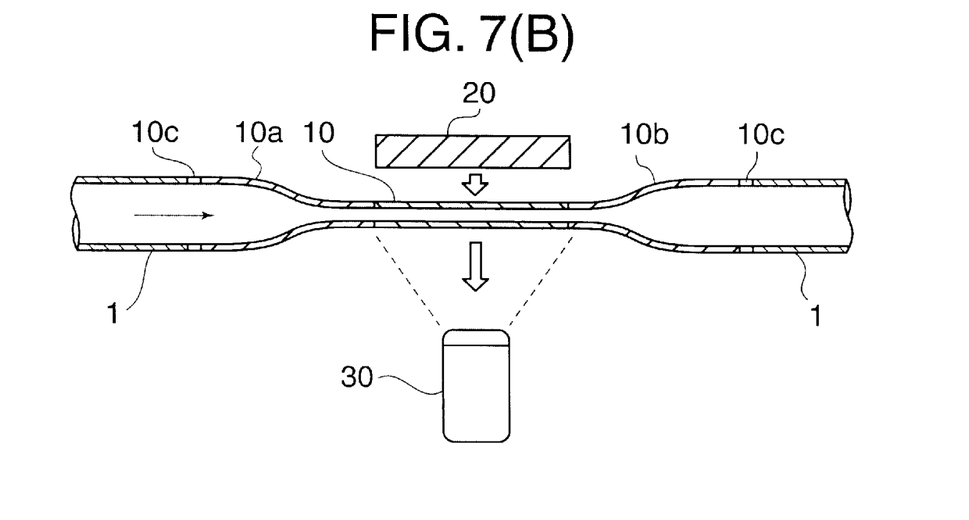

FIG. 7 illustrates an arrangement of the inspection station where the inspection window is made flat. Referring to a plant view of FIG. 7A and a partially cross sectional view of FIG. 7B, the arrangement of the inspection station will be explained.

As shown in FIGS. 7A and 7B, the inspection station joined to the conduit 1 has its inspection window 10 made of a transparent material and shaped to a flat configuration (of a four-sided thin sheet in this example) so that the cross section (across which the fluid runs) of the joint between the inspection station and the conduit 1 (including an inlet 10a and an outlet 10b shown in FIG. 7A) and of the inspection window 10 is identical to that of the conduit 1. More specifically, any of the inlet 10a, the flat shaped inspection window 10, and the outlet 10b is identical in the cross section to the conduit 1. The joint 10c comprises a common valve.

In the arrangement, integrals at the locations given by cutting the conduit 1 and the inspection window at equal intervals of a length are equal to each other. As shown in FIG. 7A, the unit time $t_n$ and the flow speed $V_n$ are expressed by $t1=t2= \ldots =t6$ and $V1=V2= \ldots =V6$. As the flow speed is constant, the trapping of foreign matter due to change of the flow speed will be avoided. Also, the inspection window shaped of a thin sheet is high in the transmission of light. Referring to FIG. 7B, the common illuminating means 20 is simply disposed opposite to the camera 30 and the system arrangement can thus be implemented at a lower cost as compared with any other system where the inspection window is illuminated in its entirety. Moreover, the imaging area is maintained flat and wide, hence increasing the accuracy of the foreign matter detection.

A method of avoiding the effect of a turbulent flow which may be generated in both the upstream and downstream sides of the inspection station will now be described. Such turbulence flows which may effect the performance of the inspection turbulence include disturbances caused by changes in the pressure and the concentration as well as the swirl described previously. When any turbulent flow occurs in the upstream of the inspection station, it may decline the accuracy of the inspection. In case that the control valve for discharging the foreign matters is provided on the downstream side of the inspection station, its opening or closing action, for example, may generate a turbulent flow which thus gives an adverse effect in the inspection station. In another instance, a turbulent flow generated at the inspection may provide an unfavorable effect in the downstream. It is hence preferable for avoiding the effect of such turbulent flow to provide a turbulence relieving tank (a balance tank).

Figure 8:
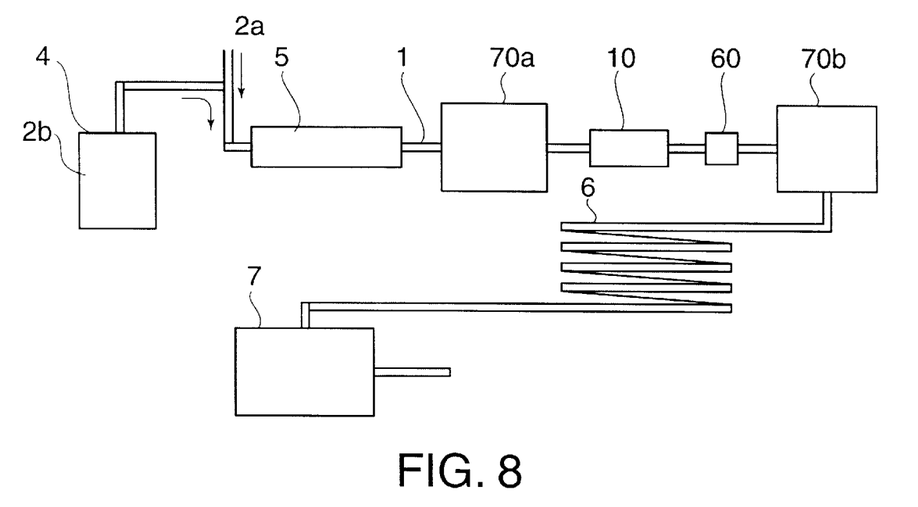
FIG. 8 is a block diagram showing a first modification of the foreign matter detecting system equipped with turbulence relieving tanks according to the present invention.
Figure 9:
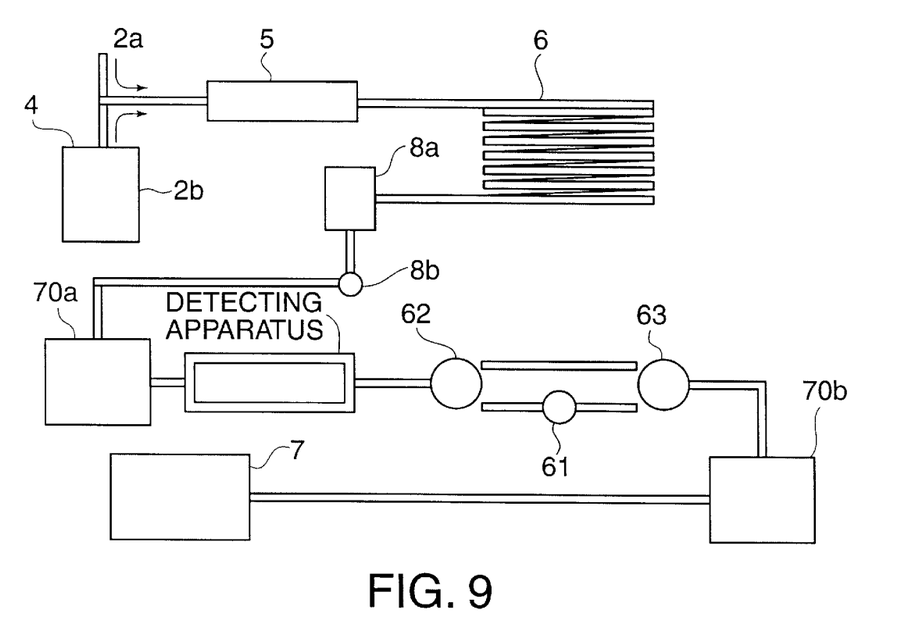
FIG. 9 is a block diagram showing a second modification of the foreign matter detecting system equipped with turbulence relieving tanks according to the present invention.

FIG. 8 is a block diagram, similar to FIG. 3, showing a first modification of the foreign matter detecting system specified with such turbulence relieving tanks, where like components are denoted by like numerals as those and will be explained in no more detail. As shown in FIG. 8, two turbulence relieving tanks 70a and 70b are provided on the upstream side and the downstream side of the inspection station (an inspection window) 10 respectively. The turbulence relieving tank 70a provided on the upstream side of the inspection station 10 receives the fluid running at a high speed in the pipeline 1 and relieves a turbulence in the flow of the fluid before releasing out the fluid to the inspection station 10. Also, the turbulence relieving tank 70b connected to the downstream side of the inspection station 10 via the control valve for discharging the foreign matter receives the fluid from the inspection station 10 and relieves a turbulence in the flow of the fluid before releasing out the fluid. This avoids declination of the accuracy of the inspection derived from the turbulence in the flow and also protects the further steps in the downstream from being affected by any turbulent flow generated at the inspection. With the arrangement shown in FIG. 4, the two turbulence relieving tanks 70a and 70b may be provided on the upstream side of the inspection station 10 and on the downstream side of a directional valve 63 respectively as shown in FIG. 9.

Figure 10:
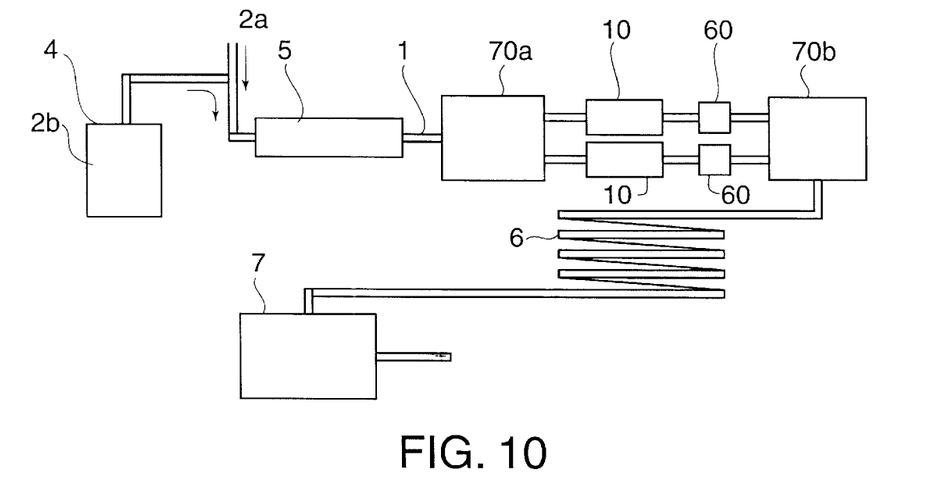
FIG. 10 is a block diagram showing a third modification of the foreign matter detecting system equipped with turbulence relieving tanks according to the present invention.

When two or more of the inspection stations 10 are connected in parallel, two turbulence relieving tanks 70a and 70b similar to those shown in FIG. 8 are provided on the upstream side and the downstream side of the inspection stations 10 respectively as shown in FIG. 10. In the foreign matter detecting system having the arrangement shown in FIG. 10, the turbulence relieving tank 70a provided on the upstream of the inspection stations 10 receives the fluid running at a high speed in the pipeline 1 and relieves a turbulence in the flow of the fluid before releasing out separate flows of the fluid to the corresponding inspection stations 10. The turbulence relieving tank 70b connected to the downstream side of the inspection stations 10 via the control valve 60 for discharging the foreign matter combines separate flows of the fluid from the inspection stations 10 to a single flow and relieves a turbulence in the flow before releasing out the fluid. This permits the turbulence relieving tank 70*a* to average the separate flows to be released out to the pipe and thus make the pressure of the fluid applied to each inspection window stable.

For example, in a production line equipped with the arrangement shown in FIG. 10 for producing a desired fluid at a speed of 20 t/h, the fluid running at 20 t/h is separated by the turbulence relieving tank 70*a* into two flows at 10 t/h which are then received by their respective inspection stations 10 for inspection. The flows of the fluid after the inspection (when foreign matters have been removed out) are then combined by the turbulence relieving tank 70*b* to a flow at 20 t/h which is thus released out. A couple of delivery pumps may be connected to the outlets of the turbulence relieving tanks 70*a* and 70*b* respectively. In addition, the turbulence relieving tanks 70*a* and 70*b* may be adapted to have a storage capacity equal or greater than that of a supply tank where the mother material for the system is stored and used as temporal storages for starting/restarting the delivery of the fluid.

As set forth above, the present invention allows a fluid material, which is conveyed in a conduit of the production line for manufacturing a liquid product such as a beverage or a liquid drug, to be inspected for removal of impurities and impurities, which are contained in each material of the product which includes materials of fiber or particle form, to be detected and automatically removed. Accordingly, the impurities which are added during the process will successfully are removed prior to the filling stage where the product is packaged into containers such as cans or bottles, hence improving the safety of the product.

Also, since the level of the analog video signal which is produced by scanning a succession of analog images with the imaging device, and a part indicative of signal is emphasized and processed, where the level of the video signal is sharply changing is compared with the reference level, the detection of minute impurities contained in the fluid which is being conveyed at a too high speed to permit the digital data processing can be carried out at real time.

Also, The analog slice level range is determined as the reference level by shifting the waveform of the analog video signal by the two different thresholds to the high and low level sides respectively. This allows the presence of foreign matter to be detected by examining whether or not the emphasized signal is within the analog slice level range, thus increasing the accuracy of the inspection. Moreover, the transparent tube segment at the inspection station is made of a illuminant for illuminating the fluid in the conduit with uniform intensity of light from different directions, thus allowing the detection of impurities at any location in the transparent tube segment and providing the more freedom of location and the ease of installation of the imaging device. Also, the inspection station of the system where the inspection window is flat and the cross section is identical to that of the conduit can hence be low in the cost and its detecting accuracy can be improved.

In the system having the two turbulence relieving tanks provided on the upstream side and the downstream side of the inspection station respectively, a change in the pressure or the concentration of the fluid produced in the upstream of the inspection station or a change in the pressure caused by the opening and closing action of the control valve at the inspection will be prevented from involving the generation of turbulence in the flow and hence declining the accuracy of the inspection. Also, no adverse effect of the turbulence in the flow will be allowed in the downstream.

What is claimed is:

1. A foreign matter detecting system for detecting a foreign matter contained in a fluid of liquid which is a subject to be inspected and is conveyed in a tubular conduit, comprising:

an inspection station which is connected to the tubular conduit and of which the inspection window for detecting foreign matter is made of at least a transparent material;

an illuminating means for illuminating the subject to be inspected with light directed through the inspection station;

an imaging means for picturing the subject to be inspected by directing an intensity of light to the inspection window and receiving transmission or reflection of the light; and a detecting means for comparing the signal level where a part indicative in which the level of the video signal is sharply changing is emphasized and processed with a reference level for the subject to be inspected to detect the foreign matter contained in the fluid.

2. A foreign matter detecting system according to claim 1, wherein a branch from the tubular conduit is connected to the downstream side of the inspection station via a control valve for discharge of the foreign matter and if the foreign matter is detected, the control valve performs an open/close action to connect the flow of the fluid to the branch for removal of a portion of the fluid in which the foreign matter is contained.

3. A foreign matter detecting system according to claim 1, wherein the reference level is a level defined in an analog slice level range which is determined by shifting the waveform of an analog video signal produced through scanning with the imaging means by two widths of threshold to both the high and low level sides respectively and the detecting means is arranged to continuously examine the analog video signal through scanning and determine whether or not the signal level after the emphasizing process is within the analog slice level range for detecting foreign matters at real time.

4. A foreign matter detecting system according to claim 1, wherein the detecting means stops output of its detection in response to a pause in the action of a filler device for filling product containers with the fluid.

5. A foreign matter detecting system according to claim 1, wherein the subject to be inspected is a liquid mixture of different materials and the inspection station is provided across the tubular conduit at the downstream of the mixing of the materials over their respective channels.

6. A foreign matter detecting system according to claim 1, wherein the inspection station including the inspection window has a cylindrical shape of which the inner diameter is identical to the inner diameter of the tubular conduit.

7. A foreign matter detecting system according to claim 6, wherein the cylindrical shaped inspection window has an annular mirror surface provided in a cross section of a wall thereof and tilted at such an angle that the intensity of light emitted from a light source is reflected on the mirror surface to linearly run throughout the wall of the cylindrical shaped inspection window, hence acting as an illuminant which illuminates with its annular mirror surface reflecting the intensity of light emitted from the light source by the illuminating means.

8. A foreign matter detecting system according to claim 6, wherein the imaging means incorporates a group of photo-sensor units arranged at equal intervals in a circle about the cylindrical shaped inspection window for allowing the detecting means to inspect the subject from different directions radically of the cylindrical shaped inspection window.

9. A foreign matter detecting system according to claim 1, wherein at least the inspection window of the inspection station is arranged flat and the cross sections at the joint to the tubular conduit and at the inspection window of the inspection station are identical to the cross section of the tubular conduit.

10. A foreign matter detecting system according to claim 1, wherein the wavelength and intensity of the light emitted from a light source of the illuminating means are predetermined corresponding to the characteristics of the subject to be inspected, and the illuminating means discharges the light having by specific wavelength and intensity based on the setting value for the subject to be inspected.

11. A foreign matter detecting system according to claim 1, wherein the illuminating means discharges the light having a plurality of wavelengths corresponding to the characteristics of the subject to be inspected.

12. A foreign matter detecting system according to claim 1, comprising a recording means to record the detection situation of impurities.

13. A foreign matter detecting system according to claim 2, wherein the duration of open/close action of the control valve is controlled based on parameters including the velocity of the fluid preset at each subjects to be inspected.

14. A foreign matter detecting system according to claim 2, wherein the duration of open/close action of the control valve is controlled with the use of a sensor which monitors and measures the current velocity of the fluid of liquid.

15. A foreign matter detecting system according to claim 7, wherein a distal portion of an optical fiber is located on the circumference of the cylindrical shaped inspection window to uniformly emit the light from its light emitting end to the annular mirror surface.

16. A foreign matter detecting system according to claim 4, further including a flow sensor which is provided adjacent to the subject to be inspected, and said flow sensor detects the pause action of the filler device based on detecting information of presence/absence of the fluid.

17. A foreign matter detecting system according to claim 1, further comprising a turbulence relieving tank provided on the upstream side of the inspection station for receiving a flow of the fluid from the upstream and relieving a turbulence in the flow before releasing out the fluid.

18. A foreign matter detecting system according to claim 1, further comprising a turbulence relieving tank provided on the downstream side of the inspection station for receiving a flow of the fluid from the inspection station and relieving a turbulence in the flow before releasing out the fluid.

19. A foreign matter detecting system according to claim 1, wherein two or more of the inspection stations are connected in parallel while a first turbulence relieving tank is provided on the upstream side of the parallelly connected inspection stations for receiving a flow of the fluid from the upstream and relieving a turbulence in the flow before delivering separate flows of the fluid to the corresponding inspection stations and a second turbulence relieving tank is provided on the downstream side of the parallelly connected inspection stations for combining flows of the fluid received from their respective inspection stations and relieving a turbulence in the flow before releasing out the fluid.

* * * * *